United States Patent
Kim et al.

(10) Patent No.: US 8,466,799 B2
(45) Date of Patent: Jun. 18, 2013

(54) APPARATUS FOR DETECTING CARBON DIOXIDE CONCENTRATION IN UNSATURATED ZONE, AND CARBON DIOXIDE CONCENTRATION MONITORING METHOD

(75) Inventors: Jeong-Chan Kim, Daejeon (KR); Ki-Sung Sung, Incheon (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 371 days.

(21) Appl. No.: 12/861,978

(22) Filed: Aug. 24, 2010

(65) Prior Publication Data
US 2011/0068940 A1    Mar. 24, 2011

(30) Foreign Application Priority Data
Sep. 21, 2009  (KR) .................. 10-2009-0089008

(51) Int. Cl.
- G08B 17/10 (2006.01)
- G01J 5/02 (2006.01)
- G01N 9/00 (2006.01)
- G06F 19/00 (2006.01)

(52) U.S. Cl.
USPC .............. 340/632; 250/343; 73/23.2; 702/24

(58) Field of Classification Search
USPC ................ 340/539.27, 601, 690, 3.31, 6.1, 340/619, 678, 3.3; 73/864.74, 1.02, 23.2, 73/23.4
See application file for complete search history.

(56) References Cited

U.S. PATENT DOCUMENTS
7,326,931 B2 *  2/2008  Frodl et al. .......... 250/343
7,520,186 B2 *  4/2009  Risk ................... 73/864.74

FOREIGN PATENT DOCUMENTS
JP     07-333129 A   * 12/1995
JP     2008-203124 A   9/2008
WO    WO2004027416 A   4/2004

OTHER PUBLICATIONS

Kominami Yasuhiro, Gas Flux Measuring Method and Apparatus, Dec. 1995, JPH07-333129 (English Translation).*

* cited by examiner

Primary Examiner — Brian Zimmerman
Assistant Examiner — Bhavin M Patel
(74) Attorney, Agent, or Firm — Chapin IP Law, LLC

(57) ABSTRACT

A system for monitoring a concentration of carbon dioxide ($CO_2$) in an unsaturated zone of a site in which $CO_2$ should be stored under the ground is provided which includes: a plurality of apparatuses for detecting the concentration of $CO_2$ in the unsaturated zone, each including a cylindrical chamber buried in an unsaturated zone under the earth surface, gas introduction holes formed in the side surface of the chamber, and a $CO_2$ concentration sensor formed through the top of the chamber so as to measure the concentration of $CO_2$ contained in the gas in the chamber; a plurality of communication devices transmitting the $CO_2$ concentration output from the $CO_2$ concentration sensor; and a monitoring server storing a reference $CO_2$ concentration every time zone and comparing the reference $CO_2$ concentration with the measured $CO_2$ concentrations transmitted from the communication devices to output a normal signal or an abnormal signal.

15 Claims, 4 Drawing Sheets

APPARATUS FOR DETECTING CARBON DIOXIDE CONCENTRATION IN UNSATURATED ZONE, AND CARBON DIOXIDE CONCENTRATION MONITORING METHOD

BACKGROUND

1. Field of the Invention

The present invention relates to carbon dioxide ($CO_2$) storage under the ground to prevent global warming, and more particularly, to a system for monitoring and alarming leakage of carbon dioxide stored under the ground which can guarantee safety of carbon dioxide storage industries or equipment on the ground by remotely monitoring leakage of carbon dioxide to a storage site or a soil in the vicinity thereof after storing carbon dioxide under the ground, and automatically issuing an alarm when carbon dioxide leaks.

2. Description of the Related Art

Carbon dioxide is the greatest reason of the global warming phenomenon, which is today the most important problem all over the world. Carbon dioxide is much contained in exhaust gas of companies running human activities, such as thermal power plants using coal for fuel, steel mills using iron ore as a raw material, and petrochemical plants using petroleum as a raw material. Therefore, to prevent the global warming phenomenon as much as possible, carbon dioxide generated for the above-mentioned reasons should be processed.

Among techniques of processing carbon dioxide, a so-called carbon dioxide underground storage technique of capturing and storing carbon dioxide under the ground attracts most attention. In the carbon dioxide underground storage technique, carbon dioxide discharged from companies and the like is captured and semi-permanently stored 800 m or more under the ground.

Carbon dioxide stored under the ground should not leak to the earth surface. However, carbon dioxide stored under the ground can leak to the earth surface for various reasons. When carbon dioxide leaks, the carbon dioxide underground storage industry may fail in spite of much cost, and the safety of ground equipment may not be guaranteed.

Therefore, it is very important to find out a stable stratum which can minimize an amount of leaking carbon dioxide stored therein. When carbon dioxide stored in the stratum leaks to the earth surface, it is necessary to construct a system which can automatically monitor the leakage of carbon dioxide, rapidly issue an alarm, and perform a post process.

SUMMARY

An advantage of some aspects of the invention is that it provides an apparatus for detecting a concentration of carbon dioxide in an unsaturated zone, which can efficiently detect the concentration of carbon dioxide in an unsaturated zone of a site in which carbon dioxide is stored under the ground.

Another advantage of some aspects of the invention is that it provides a system for monitoring a concentration of carbon dioxide in an unsaturated zone, which can automatically monitor a carbon dioxide concentration in the unsaturated zone using the apparatus for detecting carbon dioxide.

Another advantages of some aspects of the invention is that it provides a method of monitoring a concentration of carbon dioxide in an unsaturated zone, which can store a reference carbon dioxide concentration of a site in which carbon dioxide should be stored under the ground thereof, compare the reference carbon dioxide concentration with a measured carbon dioxide concentration to output a normal signal or an abnormal signal, issue an alarm to stop the storage of carbon dioxide under the ground when the abnormal signal is output.

According to an aspect of the invention, there is provided an apparatus for detecting a concentration of carbon dioxide in an unsaturated zone of a site in which carbon dioxide is stored under the ground thereof, including: a cylindrical chamber buried in an unsaturated zone under the earth surface; gas introduction holes formed in the side surface of the chamber; and a carbon dioxide concentration sensor formed through the top of the chamber so as to measure the concentration of carbon dioxide contained in the gas in the chamber.

According to another aspect of the invention, there is provided a system for monitoring a concentration of carbon dioxide in an unsaturated zone of a site in which carbon dioxide should be stored under the ground thereof, including: a plurality of apparatuses for detecting the concentration of carbon dioxide in the unsaturated zone, each including a cylindrical chamber buried in an unsaturated zone under the earth surface, gas introduction holes formed in the side surface of the chamber, and a carbon dioxide concentration sensor formed through the top of the chamber so as to measure the concentration of carbon dioxide contained in the gas in the chamber; a plurality of communication devices transmitting the carbon dioxide concentration output from the carbon dioxide concentration sensor; and a monitoring server storing a reference carbon dioxide concentration every time zone and comparing the reference carbon dioxide concentration with the measured carbon dioxide concentrations transmitted from the communication devices to output a normal signal or an abnormal signal.

According to still another aspect of the invention, there is provided a method of monitoring a concentration of carbon dioxide in an unsaturated zone of a site in which carbon dioxide is stored under the ground, the method including the steps of: (a) causing a carbon dioxide concentration detecting apparatus to measure the concentration of carbon dioxide in the unsaturated zone of the site in which carbon dioxide should be stored under the ground every time zone and to transmit the measured concentration to a monitoring server via a communication device and causing the monitoring server to store the transmitted carbon dioxide concentration as a reference carbon dioxide concentration; (b) causing the carbon dioxide concentration detecting apparatus to measure the concentration of carbon dioxide in the unsaturated zone and to transmit the measured concentration to the monitoring server via the communication device after the storage of carbon dioxide under the ground is started; and (c) causing the monitoring server to compare the measured carbon dioxide concentration with the reference carbon dioxide concentration and to output a normal signal or an abnormal signal.

Since the carbon dioxide concentration detecting apparatus according to the aspect of the invention includes a chamber and an NDIR sensor, it is possible to detect the concentration of carbon dioxide in the state where carbon dioxide in the unsaturated zone is uniform, thereby enhancing the accuracy in detection of carbon dioxide.

In the system and method of monitoring the concentration of carbon dioxide in the unsaturated zone, by measuring and storing the reference carbon dioxide concentration every time zone before storing carbon dioxide under the ground, and comparing the real-time measured carbon dioxide concentration with the reference carbon dioxide concentration, it is possible to easily distinguish a variation in carbon dioxide concentration due to an environmental variation and a variation in carbon dioxide concentration due to the leakage of carbon dioxide stored under the ground.

In the system and method of monitoring the concentration of carbon dioxide in the unsaturated zone, the carbon dioxide concentrations measured by plural carbon dioxide concentration detecting apparatuses are transmitted to the monitoring server and an alarm can be issued at once at the time of abnormality, thereby rapidly coping with the leakage of carbon dioxide stored under the ground.

DESCRIPTION OF EXEMPLARY EMBODIMENTS

Figure 1:
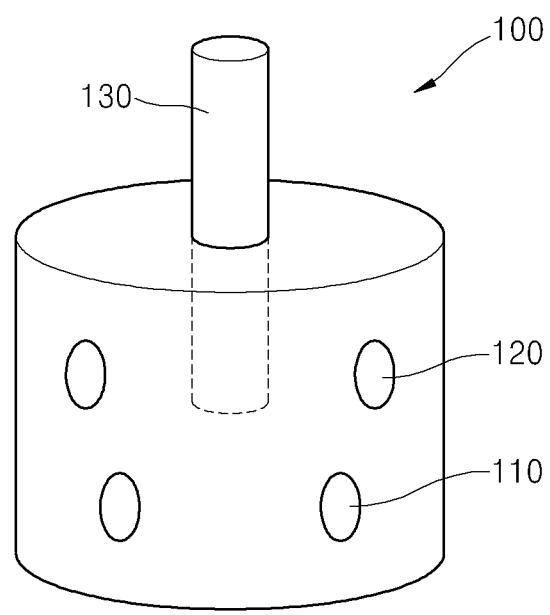
FIG. 1 is a diagram schematically illustrating an apparatus for detecting a concentration of carbon dioxide in an unsaturated zone of a site in which carbon dioxide is stored under the ground according to an embodiment of the invention.

Advantages and features of the invention and methods for putting them into practice will be apparent from the following embodiments and drawings. However, the invention is not limited to the embodiments, but can be modified in various forms. The embodiments are provided to complete the disclosure of the invention and to completely notify the scope of the invention to those skilled in the art. The invention is defined only by the appended claims. Like elements in the drawings and the specification are referenced by like reference numerals.

Hereinafter, an apparatus for detecting a carbon dioxide concentration in an unsaturated zone of a site in which carbon dioxide is stored under the ground thereof, a carbon dioxide monitoring system, and a carbon dioxide monitoring method according to an exemplary embodiment of the invention will be described in detail with reference to the accompanying drawings.

When carbon dioxide is stored under the ground, carbon dioxide flowing in the storage stratum can be checked by geophysical remote sensing. When carbon dioxide departs from the storage stratum and leaks to an undesired stratum, the leakage of carbon dioxide can be checked by the geophysical remote sensing.

By directly capturing and analyzing fluid from the underground through an observation well, it can be checked whether carbon dioxide leaks to a stratum other than the target stratum. In consideration of physical characteristics of carbon dioxide, carbon dioxide stored 800 m under the ground rises to the earth surface due to its buoyancy.

When carbon dioxide rises 800 m and reaches the earth surface, carbon dioxide leaks from the earth surface via a soil layer and an unsaturated zone.

FIG. 1 is a diagram schematically illustrating an apparatus for detecting a concentration of carbon dioxide in an unsaturated zone of a site in which carbon dioxide is stored under the ground according to an embodiment of the invention.

Referring to FIG. 1, the carbon dioxide concentration detecting apparatus 100 includes a chamber 110, gas introduction holes 120, and a carbon dioxide concentration sensor 130.

The chamber 110 has a cylindrical shape such as a circular cylinder or a square cylinder and is buried in an unsaturated zone under the earth surface. The unsaturated zone means a layer above underground water and a zone in which non-cemented rocks and soils are distributed and gas (such as oxygen, nitrogen, and carbon dioxide) and moisture coexist in the soil. The unsaturated zone is located about 50 to 100 cm below the earth surface.

The chamber 110 is formed preferably of a material not disturbing the soil layer, capable of being used for a long time, hardly reacting with gas, and not absorbing gas. The material of the chamber 110 satisfying this condition is, for example, stainless steel. Plural drain holes may be formed in the bottom of the chamber 110 so as to naturally discharge water by gravity when underground water or soil water is introduced thereto.

The gas introduction holes 120 are formed in the side surface of the chamber 110 so as to introduce gas outside the chamber 110 into the chamber 110. The gas introduction holes 120 may have a mesh shape.

The number of gas introduction holes 120 formed in the side surface of the chamber 110 may be two or more.

The carbon dioxide concentration sensor 130 are formed through the top of the chamber 110 so as to measure the concentration of carbon dioxide contained in the gas in the chamber 110.

The carbon dioxide concentration sensor 130 is preferably a non-dispersive infrared (NDIR) sensor.

Carbon dioxide in the soil can be measured by taking a gas sample in the soil and analyzing the gas sample by gas chromatography or using the NDIR sensor. The analysis of the carbon dioxide concentration in the soil using the gas chromatography takes much time and takes great human resources and cost. This analysis does not provide a time margin for rapidly coping with the increase in carbon dioxide concentration. On the other hand, the NDIR sensor is a sensor for measuring a content of carbon dioxide in the gas sample. The NDIR sensor is simple and enhances the accuracy, whereby the NDIR sensor can be preferably used.

However, when the NDIR sensor is installed in the soil, the measurement may be incomplete due to the non-uniform content of gas in solid voids. Therefore, as in the embodiment of the invention, the chamber 110 for collecting a predetermined amount of gas can be installed in the soil layer and the carbon dioxide concentration can be preferably measured from the gas, which is collected in the chamber 110 and has a uniform distribution, using the NDIR sensor.

The carbon dioxide concentration detecting apparatus 100 according to the embodiment of the invention may further include an alkaline earth metal hydroxide introduction and storage unit (not shown) in which alkaline earth metal hydroxide supplied into the chamber 110 is stored so as to react with carbon dioxide in the chamber 110 like the following chemical formula to form carbonate minerals. Here, examples of the alkaline earth metal hydroxide include $Mg(OH)_2$, $Ca(OH)_2$, and $Ba(OH)_2$.

Chemical Formula 1

$$M(OH)_2 + CO_2 \rightarrow MCO_3 + H_2O$$

(where M represents alkaline earth metal)

The alkaline earth metal hydroxide supplied to and stored in the chamber 110 reacts with carbon dioxide to form carbonate minerals. Particularly, since it is known that the content of carbon dioxide in the soil is higher about 100 times than the content of carbon dioxide in the atmospheric air, an amount of carbon dioxide sufficient for the reaction can be provided. In the alkaline earth metal hydroxide introduction and storage unit, alkaline earth metal can be introduced from the side surface of the chamber 110 and can be stored in a particularly space in the chamber 110.

The alkaline earth metal hydroxide is only stored in the alkaline earth metal hydroxide introduction and storage unit at the time of detecting the concentration of carbon dioxide and is thus isolated from the inside of the chamber 110. This is because the accuracy in detecting the concentration of carbon dioxide may be lowered when the alkaline earth metal hydroxide exists in the chamber 110 at the time of detecting the concentration of carbon dioxide.

Therefore, it is preferable that the alkaline earth metal hydroxide comes in contact with the gas in the chamber 110 except the time of detecting the concentration of carbon dioxide. For example, when the period for detecting the concentration of carbon dioxide is 1 hour, the alkaline earth metal hydroxide introduction and storage unit can communicate with the inside of the chamber for 30 minutes just after detecting the concentration of carbon dioxide.

Thanks to the alkaline earth metal hydroxide introduction and storage unit, it is possible to generate carbonate minerals and to reduce carbon dioxide, as well as to detect carbon dioxide.

Since carbon dioxide once leaking from the earth surface is mixed with the atmospheric air above the earth surface and moves rapidly, it is difficult to rapidly detect the concentration of carbon dioxide to determine the leakage and to determine whether ground equipment should be activated or deactivated. Therefore, when the concentration of carbon dioxide in an unsaturated zone just before leaking from the earth surface abnormally increases, the activation of the ground injection equipment which is injecting carbon dioxide into the underground can be temporarily stopped and the concentration and leakage of carbon dioxide can be checked to determined whether the injection should be continued.

Figure 2:
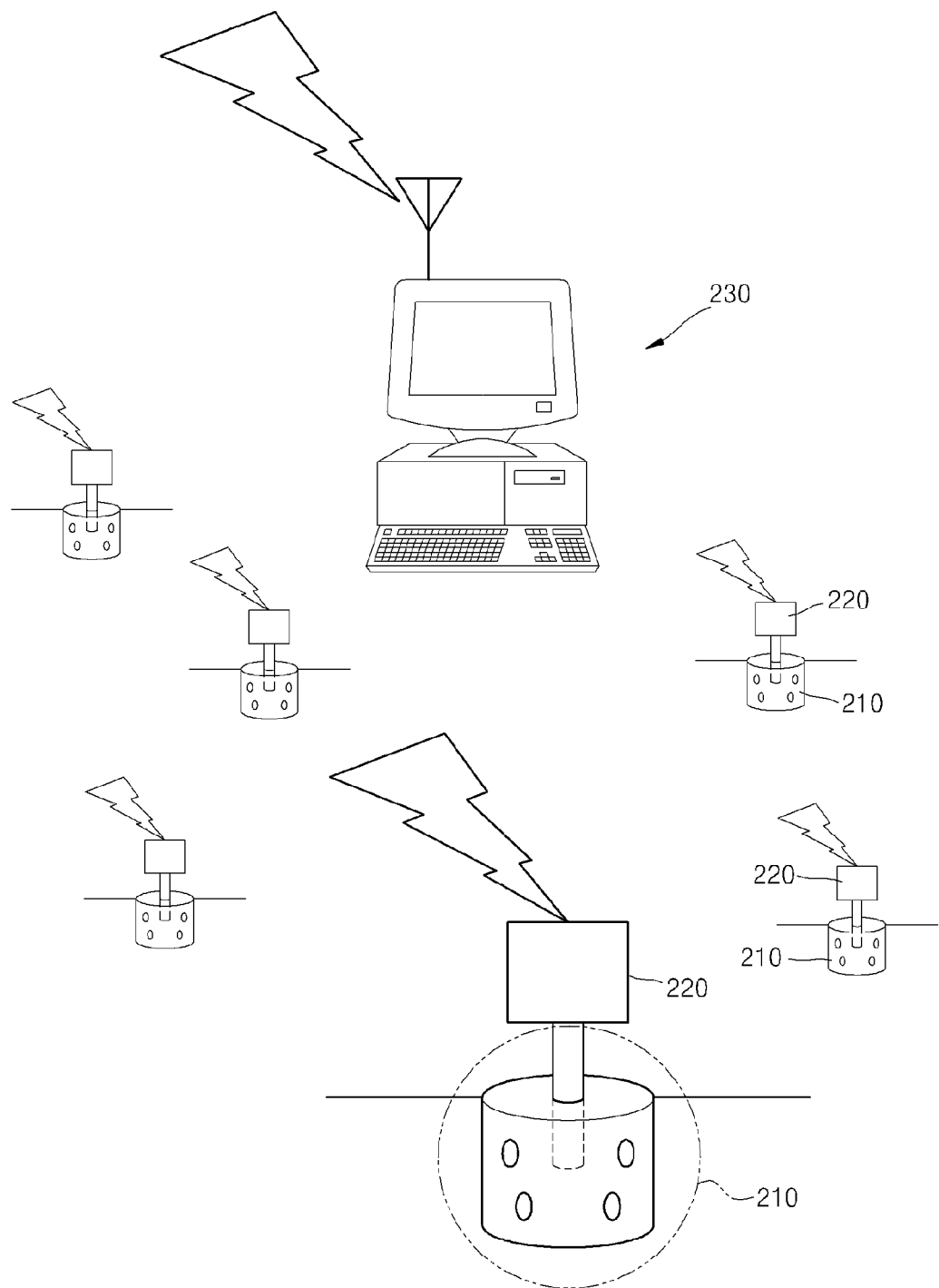
FIG. 2 is a diagram schematically illustrating a system for monitoring a concentration of carbon dioxide in an unsaturated zone of a site in which carbon dioxide is stored under the ground according to an embodiment of the invention.

FIG. 2 is a diagram schematically illustrating a system for monitoring a concentration of carbon dioxide in an unsaturated zone of a site in which carbon dioxide is stored under the ground according to an embodiment of the invention.

Referring to FIG. 2, the shown carbon dioxide concentration monitoring system includes plural carbon dioxide concentration detecting devices 210, plural communication devices 220, and a monitoring server 230.

The plural carbon dioxide concentration detecting devices 210 each include a chamber, gas introduction holes, and a carbon dioxide concentration sensor.

The chamber is formed of a material such as stainless steel, is buried in the unsaturated zone under the earth surface, and has a cylindrical shape.

The gas introduction holes are formed in a mesh shape in the side surface of the chamber so as to introduce ambient gas into the chamber.

The carbon dioxide concentration sensor is formed through the top of the chamber so as to measure the concentration of carbon dioxide contained in the gas in the chamber. The carbon dioxide concentration sensor is preferably the NDIR sensor.

The chamber, the gas introduction holes, and the carbon dioxide concentration sensor of the plural carbon dioxide concentration detecting devices 210 are the same as described with reference to FIG. 1, and their details will not be described.

On the other hand, carbon dioxide temporary storage equipment, pressurizing equipment, temperature-raising equipment, injection equipment, and the like are disposed in a carbon dioxide storage site. In consideration of these equipment, the carbon dioxide storage site may have an area of 200 m×200 m or more.

Therefore, plural carbon dioxide concentration detecting devices 210 are disposed in the carbon dioxide storage site. Since carbon dioxide may leak to the periphery of the storage site, the carbon dioxide concentration detecting devices 210 are preferably disposed in the periphery of the carbon dioxide storage site, as well as the carbon dioxide storage site.

The plural communication devices 220 are connected to the carbon dioxide concentration sensors of the carbon dioxide concentration detecting devices 210 and transmit the carbon dioxide concentrations output from the carbon dioxide concentration sensors to the monitoring server 230 by wireless communication. In this embodiment, a wireless communication device is exemplified as carbon dioxide concentration transmitting means, which is convenient when remote or plural carbon dioxide concentration devices 210 are provided. This does not mean any exclusion of a wired communication device.

The monitoring server 230 stores a reference carbon dioxide concentration every time zone. The monitoring server 230 compares the reference carbon dioxide concentration $C\_ref$ stored in advance with the measured carbon dioxide concentration $C\_detec$ transmitted from the communication device 220 and outputs a normal signal or abnormal signal from a monitor or a printer. The monitoring server 230 may directly output the measured carbon dioxide concentration and may store the measured carbon dioxide concentration in a storage space thereof.

The monitoring server 230 can compare the measured carbon dioxide concentration $C\_detec$ with the reference carbon dioxide concentration $C\_ref$ corresponding to the measuring time, and can generate the abnormal signal when the measured carbon dioxide concentration $C\_detec$ is greater by a predetermined value or more than the reference carbon dioxide concentration $C\_ref$.

The monitoring server 230 may generate the abnormal signal when the measured carbon dioxide concentration $C\_detec$ is greater by a specific numerical value $\alpha$ or more than the reference carbon dioxide concentration $C\_ref$ ($C\_detec \geq C\_ref + \alpha$).

The monitoring server 230 may generate the abnormal signal when the measured carbon dioxide concentration $C\_detec$ is equal to or greater than a specific ratio $\beta\%$ (where $\beta$ is greater than 1) of the reference carbon dioxide concentration $C\_ref$ ($C\_detec \geq \beta \times C\_ref$).

Figure 3:
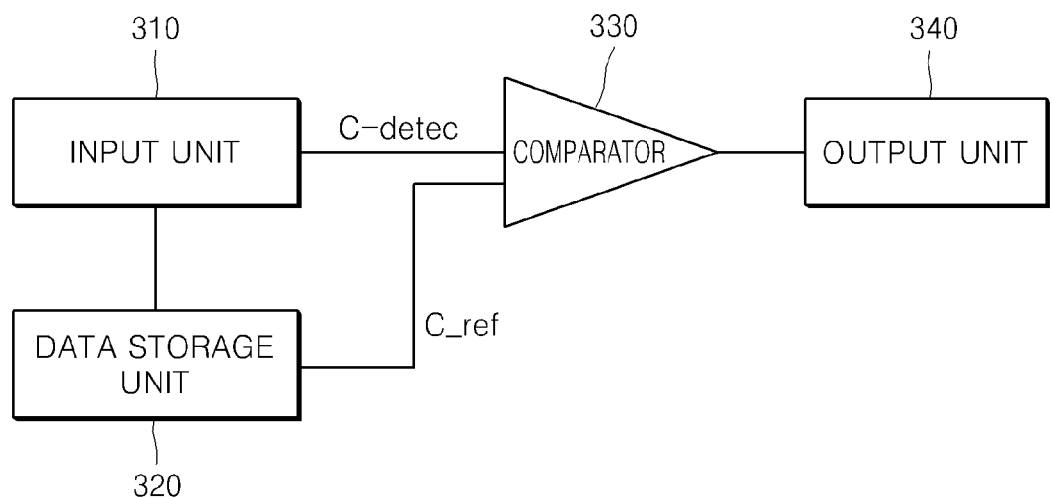
FIG. 3 is a diagram schematically illustrating the configuration of a monitoring server shown in FIG. 2.

To perform the above-mentioned operations, the monitoring server 230 includes an input unit 310, a data storage unit 320, a comparison unit 330, and an output unit 340, as shown in FIG. 3.

The input unit 310 receives the measured carbon dioxide concentration $C\_detec$ from each communication device of the carbon dioxide concentration detecting devices 210. The data storage unit 320 stores the reference carbon dioxide concentration every time zone.

The comparison unit 330 receives the measured carbon dioxide concentration $C\_detec$ from the input unit 310, receives the reference carbon dioxide concentration $C\_ref$ from the data storage unit 320, compares the measured carbon dioxide concentration $C\_detec$ with the reference carbon dioxide concentration $C\_ref$, and outputs a result signal such as "0" or "1" and "LOW" or "HIGH".

The output unit 340 outputs a normal signal or an abnormal signal to an output device such as a monitor or a printer on the basis of the result signal from the comparison unit 330.

On the other hand, the monitoring server 230 may be connected to an alarm device (not shown). The alarm device can issue an alarm such as a siren so as to cause a manager or an operator to recognize the leakage of carbon dioxide.

Figure 4:
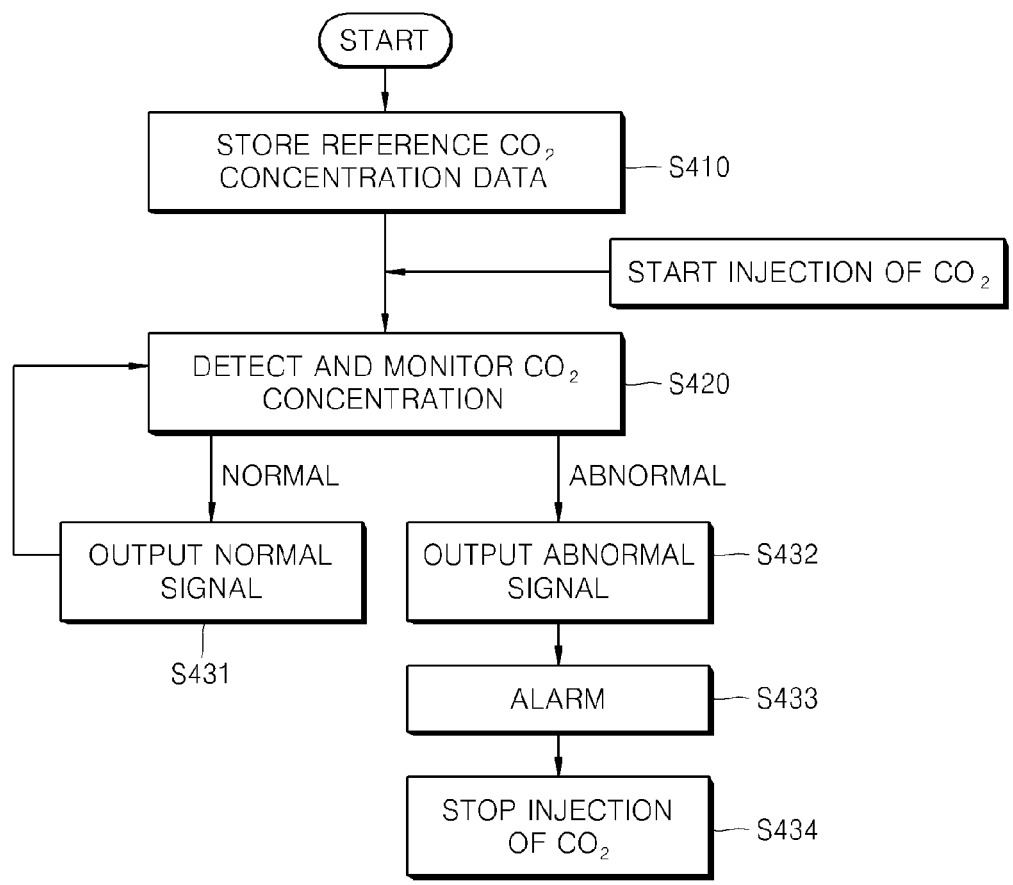
FIG. 4 is a flowchart illustrating a method of monitoring a concentration of carbon dioxide in an unsaturated zone of a site in which carbon dioxide is stored under the ground according to an embodiment of the invention.

FIG. 4 is a flowchart illustrating a method of monitoring a concentration of carbon dioxide in an unsaturated zone of a site in which carbon dioxide is stored under the ground according to an embodiment of the invention.

Referring to FIG. 4, the shown carbon dioxide concentration monitoring method includes a reference carbon dioxide concentration data storing step S410, a carbon dioxide concentration detecting and monitoring step S420, and a result signal output step S431 and S432.

In the reference carbon dioxide concentration data storing step S410, the carbon dioxide concentration detecting device measures the concentration of carbon dioxide in the unsaturated zone of the site in which carbon dioxide should be stored under the ground every time zone and transmits the measured concentration to the monitoring server via the communication device, and the monitoring server stores the transmitted carbon dioxide concentration as a reference carbon dioxide concentration.

As shown in FIG. 1, the carbon dioxide concentration detecting device may include a cylindrical chamber buried in an unsaturated zone under the earth surface, gas introduction holes formed in the side surface of the chamber, and a carbon dioxide concentration sensor formed through the top of the chamber so as to measure the concentration of carbon dioxide contained in the gas in the chamber.

The reason for storing the reference carbon dioxide concentration in advance is as follows.

Carbon dioxide in the soil or the unsaturated zone varies in concentration depending on biological activities in the soil and physical phenomena influencing the activities. It is known that the content of carbon dioxide in the soil is higher by about 100 times than the content of carbon dioxide in the atmospheric air due to decomposition and oxidation of organics. The concentration of carbon dioxide in the soil frequently varies depending on seasons, day and night, and other physical chemical conditions. Since the concentration of carbon dioxide varies in zones depending on the characteristics of the soil, the depth of the soil layer, and the moisture content and varies by several meters, it is very difficult to generalize the concentration of carbon dioxide in the soil. Therefore, to check whether the injected carbon dioxide leaks, it is necessary to measure the concentration of carbon dioxide at a predetermined position every time zone for 1 year or more to see a natural background concentration, and to cope with the abnormality when an abnormal value departing from the background concentration is measured.

That is, after sufficiently studying the characteristic of the carbon dioxide concentration and the factors causing the variation in concentration by days, months, quarters, and seasons, it is preferable that the natural variation and the other variations are distinctly coped with.

In the carbon dioxide concentration detecting and monitoring step S420, after the storage of carbon dioxide under the ground is started, the carbon dioxide concentration detecting device measures the concentration of carbon dioxide in the unsaturated zone and transmits the measured concentration to the monitoring server via the communication device, and the monitoring server compares the measured carbon dioxide concentration with the reference carbon dioxide concentration.

In the result signal output step S431 and S432, the monitoring server outputs a normal signal or an abnormal signal on the basis of the comparison result of the measured carbon dioxide concentration with the reference carbon dioxide concentration. The monitoring server may compare the measured carbon dioxide concentration with the reference carbon dioxide concentration and may generate the abnormal signal when the measured carbon dioxide concentration is greater by a predetermined value or more than the reference carbon dioxide concentration.

When the abnormal signal is output from the monitoring server, the method may further include a step S433 of issuing an alarm so as to stop the injection of carbon dioxide (S434).

As described above, in the system and method of monitoring the concentration of carbon dioxide in the unsaturated zone according to the embodiment of the invention, by measuring and storing the reference carbon dioxide concentration every time zone before storing carbon dioxide under the ground, and comparing the real-time measured carbon dioxide concentration with the reference carbon dioxide concentration, it is possible to easily distinguish a variation in carbon dioxide concentration due to the environmental variation and a variation in carbon dioxide concentration due to the leakage of carbon dioxide stored under the ground. Since the carbon dioxide concentration detecting apparatus includes the chamber and the NDIR sensor, it is possible to detect the concentration of carbon dioxide in the state where carbon dioxide in the unsaturated zone is uniform, thereby enhancing the accuracy in detection of carbon dioxide.

In the system and method of monitoring the concentration of carbon dioxide in the unsaturated zone according to the embodiment of the invention, the measured carbon dioxide concentration can be transmitted to the monitoring server in real time and an alarm can be issued at once at the time of outputting an abnormal signal, thereby rapidly coping with the leakage of carbon dioxide stored under the ground.

The specific embodiment of the invention has been described, but the invention can be modified in various forms by those skilled in the art. The invention includes the modifications without departing from the scope of the invention. Therefore, the scope of the invention is defined by the appended claims.

What is claimed is:

1. An apparatus for detecting a concentration of carbon dioxide in an unsaturated zone of a site in which carbon dioxide is stored under the ground thereof, comprising:
   a cylindrical chamber buried in an unsaturated zone under the earth surface;
   gas introduction holes formed in the side surface of the chamber;
   a carbon dioxide concentration sensor formed through the top of the chamber so as to measure the concentration of carbon dioxide contained in the gas in the chamber; and
   an alkaline earth metal hydroxide introduction and storage unit formed on the side surface of the chamber so as to store alkaline earth metal hydroxide supplied from the chamber.

2. The apparatus according to claim 1, wherein the carbon dioxide concentration sensor is a non-dispersive infrared (NDIR) sensor.

3. The apparatus according to claim 1, wherein the gas introduction holes have a mesh shape.

4. The apparatus according to claim 1, wherein the alkaline earth metal hydroxide includes at least one of $Mg(OH)_2$, $Ca(OH)_2$, and $Ba(OH)_2$.

5. The apparatus according to claim 1, wherein the chamber is formed of stainless steel.

6. A system for monitoring a concentration of carbon dioxide in an unsaturated zone of a site in which carbon dioxide should be stored under the ground thereof, comprising:

a plurality of apparatuses for detecting the concentration of carbon dioxide in the unsaturated zone, each including a cylindrical chamber buried in an unsaturated zone under the earth surface, gas introduction holes formed in the side surface of the chamber, and a carbon dioxide concentration sensor formed through the top of the chamber so as to measure the concentration of carbon dioxide contained in the gas in the chamber;

a plurality of communication devices transmitting the carbon dioxide concentration output from the carbon dioxide concentration sensor;

a monitoring server storing a reference carbon dioxide concentration every time zone and comparing the reference carbon dioxide concentration with the measured carbon dioxide concentrations transmitted from the communication devices to output a normal signal or an abnormal signal; and an alkaline earth metal hydroxide introduction and storage unit formed on the side surface of the chamber so as to store alkaline earth metal hydroxide supplied from the chamber.

7. The system according to claim 6, further comprising an alarming device issuing an alarm in response to the abnormal signal from the monitoring server.

8. The system according to claim 6, wherein the monitoring server compares the reference carbon dioxide concentration with the measured carbon dioxide concentration and generates the abnormal signal when the measured carbon dioxide concentration is greater by a predetermined value or more than the reference carbon dioxide concentration.

9. The system according to claim 8, wherein the monitoring server generates the abnormal signal when the measured carbon dioxide concentration is greater by a predetermined numerical value or more than the reference carbon dioxide concentration.

10. The system according to claim 8, wherein the monitoring server generates the abnormal signal when the measured carbon dioxide concentration is equal to or greater than a predetermined ratio of the reference carbon dioxide concentration.

11. The system according to claim 6, wherein the monitoring server includes:

an input unit receiving the measured carbon dioxide concentration from the communication devices;

a data storage unit storing the reference carbon dioxide concentration every time zone;

a comparison unit comparing the measured carbon dioxide concentration with the reference carbon dioxide concentration; and an output unit outputting the normal signal or the abnormal signal on the basis of the comparison result of the comparison unit.

12. The system according to claim 6, wherein the carbon dioxide concentration sensor is a non-dispersive infrared (NDIR) sensor.

13. The system according to claim 6, wherein the gas introduction holes have a mesh shape.

14. The system according to claim 6, wherein the alkaline earth metal hydroxide includes at least one of $Mg(OH)_2$, $Ca(OH)_2$, and $Ba(OH)_2$.

15. The system according to claim 6, wherein the chamber is formed of stainless steel.

* * * * *